United States Patent
McMichael

(10) Patent No.: US 7,101,847 B2
(45) Date of Patent: Sep. 5, 2006

(54) METHOD OF TREATING CHRONIC PELVIC PAIN SYNDROME BY ADMINISTRATION OF CHORIONIC GONADOTROPIN

(75) Inventor: John McMichael, Delanson, NY (US)

(73) Assignee: Milkhaus Laboratory, Inc., Providence, RI (US)

( * ) Notice: Subject to any disclaimer, the term of this patent is extended or adjusted under 35 U.S.C. 154(b) by 452 days.

(21) Appl. No.: 10/446,254

(22) Filed: May 28, 2003

(65) Prior Publication Data

US 2004/0072731 A1      Apr. 15, 2004

Related U.S. Application Data

(60) Provisional application No. 60/417,878, filed on Oct. 11, 2002.

(51) Int. Cl.
*A61K 38/16*  (2006.01)
*A61K 38/24*  (2006.01)

(52) U.S. Cl. ............................................ 514/8; 514/12
(58) Field of Classification Search .................... None
See application file for complete search history.

(56) References Cited

U.S. PATENT DOCUMENTS

| 4,016,250 | A |   | 4/1977  | Saxena |
| 4,692,332 | A |   | 9/1987  | McMichael |
| 5,610,136 | A | * | 3/1997  | McMichael ................... 514/8 |
| 5,629,318 | A |   | 5/1997  | Gormley et al. |
| 6,054,455 | A |   | 4/2000  | Guess et al. |
| 6,495,668 | B1 |  | 12/2002 | Gilbert et al. |
| 2003/0124620 | A1 | | 7/2003 | Seifer et al. |

OTHER PUBLICATIONS

Howard, FM Chronic Pelvic Pain. Obstet Gynecol. 2003. Mar; 101(3): 594-611. Abstract.*
Nickel, JC. Interstitial cystitis: a chronic pelvic pain syndrome. Med Clin North Am. 2004. Mar; 88: 467-81, xii.*
*International Search Report* corresponding to International Patent Application Serial No. PCT/US03/16984, ISA/US dated Oct. 30, 2003, 5 pages.
Collins et al., "How Common is Prostatitis? A National Survey of Physician Visits," *J. Urology*, 159:1224-1228 (1998).

* cited by examiner

*Primary Examiner*—Marianne P. Allen
*Assistant Examiner*—Ian Dang
(74) *Attorney, Agent, or Firm*—Marshall Gerstein & Borun LLP

(57) ABSTRACT

The present invention is directed to methods of treating a chronic pelvic pain syndrome comprising the step of administering to a subject suffering from prostatis a chorionic gonadotropin or a pharmaceutically active fragment or derivative thereof in an amount effective to alleviate one or more symptoms of a chronic pelvic pain syndrome.

6 Claims, No Drawings

METHOD OF TREATING CHRONIC PELVIC PAIN SYNDROME BY ADMINISTRATION OF CHORIONIC GONADOTROPIN

RELATED APPLICATIONS

This application claims benefit of co-pending U.S. Provisional Patent Application Ser. No. 60/417,878, which was filed Oct. 11, 2002.

BACKGROUND OF THE INVENTION

The present invention relates to treatment of symptoms of chronic pelvic pain syndromes generally inclusive of syndromes such as prostatis.

Prostatitis and prostatodynia are extremely prevalent diseases in men (Collins M M, et al., "How common is prostatitis? A national survey of physician visits," Journal of Urology, 159:1224–1228 (1998)). There are more outpatient visits for prostatitis than for benign prostatic hypertrophy (BPH) or prostate cancer. Although the epidemiologic evidence is limited, it appears that the prevalence of prostatitis is approximately 2–9% in adult men. It has been suggested that 35–50% of men are affected by prostatitis at some time in life. Based on the National Ambulatory Medical Care Surveys from 1990–1994, approximately 2 million ambulatory visits are made annually for prostatitis. This accounts for 8% of all visits to urologists and 1% of all visits to primary care physicians. Many men remain symptomatic for much of their lives.

Chronic pelvic pain syndrome encompasses a variety of related syndromes including prostatitis and can be characterized by evidence of prostatic inflammation and by the presence or absence of white blood cells in prostatic fluid and/or pain associated with the prostate. This inflammation of the prostate causes pain in the abdomen, testicles, or tip of the penis, urination problems, and painful ejaculation. Its cause often cannot be determined. Bacteria are usually not detected in the urine. Fever, chills, or other signs of an infection are not present. Within this group of syndromes, the origins of chronic idiopathic prostatitis, asymptomatic prostatitis, and prostatodynia are problematic and are probably the least understood. The origin of these diseases has been attributed to some undefinable bacterial or viral infection, but this has never been proven. These syndromes do not exist prior to puberty but have a peak incidence between the ages of 18 and 50. It is possible that these three specific entities actually represent the same disease process in different phases or forms. Suggestions as to the origins of these conditions have included a chemical imbalance in the prostate, infection undetected by current microbiological methods, and autoimmunity to the prostate gland itself.

The causes of noninflammatory chronic pelvic pain syndrome may be the same as those for inflammatory chronic pelvic pain syndrome. Some doctors think that the prostate may not be involved at all but that a combination of things, including nervous system problems, strained pelvic floor muscles, and emotional factors cause the pain.

Chronic nonbacterial prostatitis is an inflammatory and pain condition of unknown etiology characterized by excessive inflammatory cells in prostatic secretions despite no history of documented urinary tract infection and negative bacterial cultures of urine and prostatic secretions. Chronic nonbacterial prostatitis is even more common than bacterial prostatitis. Symptoms simulate those of chronic bacterial prostatitis and these patients usually show an increase in the number of white blood cells and oval fat bodies in their expressed prostatic secretions. However, they rarely have a history of urinary tract infection, and lower-tract localization cultures fail to reveal a pathogenic organism. Patients with prostatodynia have negative bacterial cultures, normal prostatic secretions, and no history of urinary tract infection. Symptoms of chronic nonbacterial prostatitis and prostatodynia vary but include urinary urgency and frequency, nocturia, dysuria, and pain and discomfort perceived in the pelvic, suprapubic, or genital area. Sometimes postejaculatory pain and discomfort are prominent features. Physical findings for both conditions are nonspecific.

This condition has recently been reclassified into two major subtypes, inflammatory chronic pelvic pain syndrome ($CPIII_A$ presence of leucocytes in the post-prostate massage urine sample); and non-inflammatory chronic pelvic pain syndrome ($CPIII_B$ formerly termed prostatodynia) a painful prostate in which no infection or inflammation is present.

The etiology of the condition has, to date, not been fully elucidated. Research has focused on finding sub-clinical relationships to several infectious disease pathogens as well as non-infectious disease entities such as neuromuscular dysfunction of the bladder neck or uro-genital diaphragm, allergies, psychological, and autoimmune vectors. To date therapeutic approaches to this condition remains, for the most part, ineffective.

Chronic pelvic pain syndrome which represents about 90% of men with prostatis is distinguished from those caused by bacterial infection which include acute bacterial prostatitis (also known as Category I prostatitis) which is a serious infection in the prostate and which causes severe symptoms. Acute bacterial prostatitis is treatable by antibiotics, pain and fever medication, stool softeners, fluids and rest.

Chronic pelvic pain syndrome is also distinguished from chronic bacterial prostatitis (also known as Category II prostatis) which represents a more resistant infection requiring longer term therapy can occur more often in men who have had repeated urinary tract infections. Infected prostatic caleuli (stones) can make the infection more difficult to cure and may require surgical removal. Surgery may also be required if urinary tract problems such as narrowing of the bladder neck or urethra are causing the problems.

Noninflammatory chronic pelvic pain is extremely difficult to treat because its cause is unknown. The primary goal of treatment is to relieve symptoms. Non-narcotic pain medications, muscle relaxers, and alpha-blockers are used. Physical therapy, medications to reduce anxiety, exercise, massage therapy, biofeedback, or stress reduction may help some men. Home treatment may also be helpful in relieving the symptoms.

Of interest to the present invention is the disclosure of Guess et al., U.S. Pat. No. 6,054,455 which is directed to methods for treatment or prevention of chronic nonbacterial prostatitis and prostadynia by administration of tachykinin receptor antagonist is a neurokinin-1 receptor antagonist. Also of interest is the disclosure of Gormley, et al., U.S. Pat. No. 5,629,318 which is directed to a method for treatment of chronic prostatitis with 17.beta.-N-monosubstituted-carbamoyl-4-aza-5.alpha.-androst-1-en-3-one compounds such as testosterone-5.alpha.-reductase inhibitors for the treatment of chronic prostatitis. Despite these and other treatments for chronic pelvic pain syndromes there remains a need in the art for improved treatment methods.

Nevertheless, there are currently no established treatments for chronic nonbacterial prostatitis or prostatodynia. Antibiotics are often prescribed empirically, but with little evidence of efficacy. Alpha blockers are sometimes prescribed for prostatodynia, but their efficacy has not been established. Patients who respond poorly to medical management or have significant emotional problems are referred for psychiatric intervention. Hot sitz baths and anticholinergic drugs are generally employed to provide some symptomatic relief, as is periodic prostatic massage. Accordingly, there remains a need in the art for improved methods for treatment of chronic pelvic pain syndromes.

Of interest to the present invention is the disclosure of McMichael, U.S. Pat. No. 4,692,332 which relates to the use of equine chorionic gonadotropin and human chorionic gonadotropin (hCG) in combination with an immune enhancer such as a lysate of Staphylococcus aureus for treatment of malignant neoplasia. The mechanism of action in the treatment of the cancer was proposed to involve chorionic gonadotropin as a signal molecule capable of inducing apoptosis via membrane changes on the transformed cell at the molecular level, or alternatively by altering the electrical charge of the transformed cell to render it more susceptible to immune elimination. This patent further taught the need to stimulate the cell mediated immune response so that necrotic debris associated with tumor reduction could be efficiently phagocytized to prevent a potentially fatal Herxheimer-type reaction. U.S. Pat. No. 4,692,332, however, fails to disclose the use of chorionic gonadotropin for treatment of non-neoplastic states such as benign prostatic hypertrophy.

Also of interest to the present invention is the disclosure of McMichael, U.S. Pat. No. 5,610,136 which discloses methods of treating benign prostatic hypertrophy by administration of a chorionic gonadotropin or a pharmaceutically active fragment or derivative thereof. hCG, a signaling molecule, is thought to induce apoptosis (cellular death) via membrane changes and down regulation of the BCL2 at the genomic level rendering the cell susceptible to apoptosis. This may be likened to a negative feedback signal and be similar to cutaneous immunization for allergic reactions. At optimal concentrations hCG reduces the tendency for uncontrolled cell proliferation which occurs in abnormal accelerated cellular-growth conditions such as benign prostatitic hypertrophy (BPH).

SUMMARY OF THE INVENTION

The present invention provides methods for treatment of symptoms of chronic pelvic pain syndrome by administration of effective amounts of chorionic gonadotropins and effective fragments and derivatives thereof including but not limited to the beta subunit of chorionic gonadotropin and effective derivatives and fragments thereof. Effective amounts include preferably range from dosages of from 0.02 to 200 International units per dosage when administered sublingually up to four times daily with dosage ranges of from 0.2 to 20 International Units being particularly preferred and a dosage unit of 2 International Units of human chorionic gonadotropin (hCG) being particularly preferred when administered sublingually four times daily and particularly so when administered in the form of sublingual drops. While human chorionic gonadotropin (which may be derived naturally or recombinantly) is particularly preferred, other chorionic gonadotropins including equine chorionic gonadotropin may be used according to the methods of the invention.

The methods of the invention are directed to treatment of symptoms of various chronic pelvic pain syndromes, however defined, including chronic prostatitis and as well as the symptoms of inflammatory chronic pelvic pain syndrome and non-inflammatory pelvic pain syndrome. Such symptoms include but are not limited to pain in the abdomen, pelvic area, suprapubic area or genital area including testicles, or tip of the penis, and the like. Other symptoms include urinary problems including urinary urgency and frequency, nocturia, dysuria and sexual dysfunction including painful ejaculation.

DETAILED DESCRIPTION

The present invention provides methods for the treatment of symptoms of chronic pelvic pain syndromes including but not limited to perineal and pelvic pain or discomfort, difficulty in voiding and erectile dysfunction.

Without being bound by any theory of the invention it is believed that chorionic gonadotropins act as signaling molecules and may induce apoptosis via membrane changes and down regulation of the BCL2 gene at the genomic level thus rendering cells susceptible to apoptosis. This may be likened to a negative feed back signal and may be similar to cutaneous immunization for allergic reactions. Administration of chorionic gonadotropins at optimal concentrations reduces the tendency for uncontrolled cell proliferation which results in abnormal accelerated cellular-growth conditions including cancers and benign prostatic hypertrophy (BPH). While the exact mechanism of action is not understood with respect to chronic pelvic pain syndromes, it is similar mechanisms may be implicated in an as yet unknown way.

The compositions are preferably administered as sublingual drops in dosages ranging from about 0.2 International Units to 20 International Units with dosages of about 2 International Units of human chorionic gonadotropin per dosage four times daily being preferred as the initial treatment dosage. After an initial therapeutic effect has been noted, preferred dosages comprise about 2 International Units of human chorionic gonadotropin per dosage once or twice daily. While the compositions of the invention are preferably administered as sublingual drops, it is contemplated that they may be administered by other means known to the art including but not limited to oral administration, injection, and transdermal administration. When administered in the form of sublingual drops, the compositions preferably comprise single drops (approximately 0.05 ml) of hCG at a concentration of 40 International Units per mL in 0.9% saline.

EXAMPLE 1

According to this example, three subjects presented with chronic prostatis and were treated by sublingual administration four times daily of one drop (0.05 mL) of a formulation comprising 2 International Units of human chorionic gonadotropin (hCG) in 0.9% saline. After four weeks, all three of the test subjects reported a positive response without adverse effects.

EXAMPLE 2

According to this example an open-label clinical trial was carried out in which 17 subjects diagnosed with chronic prostatis or chronic pelvic pain syndrome were treated according to the invention. These subjects presented with disease symptoms experienced for greater than 3 months in the absence of infection and had at least a moderate score of the National Institutes of Health Chronic Prostatitis Symptom Index (CPSI) with an overall score of greater than 15 out of a potential 0–43 points. The CPSI makes a subjective evaluation of three categories of symptoms including pain or discomfort, urination, and impact of symptoms/quality of life.

With the exception of antibiotics, systemic chemotherapy, and NSAIDS, the subjects discontinued all previous therapy, prescribed or not, for Chronic Nonbacterial Prostatitis/Chronic Pelvic Pain Syndrome, for at least 14 days and must not have had evidence of side effects from previous therapy. Patients must have discontinued the use of antibiotics, systemic chemotherapy, and NSAIDs at least 30 days prior to the first study drug administration.

The subjects were treated by sublingual administration of one drop (0.05 mL) of a formulation comprising 2 International Units of hCG four times daily for 12 weeks and were evaluated for compliance, safety, and efficacy at weeks 4, 8 and 12. Evaluation of the subjects by the NIH CPSI showed that the average total score for all patient subjective measurements progressively improved from baseline levels during the course of the study. Specifically, the CPSI scores improved from a baseline mean of 23.4 to a mean of 11.7 (50% improvement) for the eight subjects who first completed 12 weeks of therapy at 12 weeks of therapy. In addition the most responsive sub-category in a Chronic Pelvic Pain Symptom Source was the pain component which showed a 68% improvement in responsiveness. The treatment results also exhibited a 58% improvement in sexual function over twelve weeks.

Numerous modifications and variations of the above-described invention are expected to occur to those of skill in the art. Accordingly, only such limitations as appear in the appended claims should be placed thereon.

What is claimed:

1. A method of treating a chronic pelvic pain syndrome comprising the step of administering to a subject suffering therefrom a chorionic gonadotropin in an amount effective to alleviate one or more symptoms of said syndrome wherein the syndrome is chronic prostatitis.

2. The method of claim 1 wherein the chorionic gonadotropin is selected from the group consisting of human and equine chorionic gonadotropins.

3. The method of claim 2 wherein the choriome gonadotropin is human chorionic gonadotropin.

4. The method of claim 1 wherein the chorionic gonadotropin is administered in a dosage ranging from 0.2 International Units to 20 International Units.

5. The method of claim 1 wherein the chorionic gonadotropin dosage is administered from one to four times daily.

6. The method of claim 1 wherein the dosage is administered in the form of sublingual drops.

* * * * *

UNITED STATES PATENT AND TRADEMARK OFFICE
CERTIFICATE OF CORRECTION

PATENT NO.      : 7,101,847 B2
APPLICATION NO. : 10/446254
DATED           : September 5, 2006
INVENTOR(S)     : John McMichael Page 1 of 1

It is certified that error appears in the above-identified patent and that said Letters Patent is hereby corrected as shown below:

At Column 6, line 18, please delete "choriome" and insert -- chorionic --.

Signed and Sealed this

Ninth Day of January, 2007

JON W. DUDAS
*Director of the United States Patent and Trademark Office*